United States Patent [19]

Dedieu et al.

[11] Patent Number: 4,698,298

[45] Date of Patent: Oct. 6, 1987

[54] COMPETITIVE IMMUNOASSAY PROTOCAL FOR TARGETS INCLUDING LIPOPROTEINS AND ALPHA-FETOPROTEIN

[75] Inventors: Alain Dedieu, Avignon; Campbell Lockhart; Etienne Jolu, both of Bagnols sur Cèze, all of France

[73] Assignee: Commissariat a l'Energie Atomique, Paris, France

[21] Appl. No.: 596,386

[22] Filed: Apr. 3, 1984

[51] Int. Cl.⁴ ............... G01N 33/53; G01N 33/535; G01N 33/545; G01N 33/574
[52] U.S. Cl. ..................... 435/7; 435/188; 435/810; 436/531; 436/548; 436/804; 436/808; 436/810; 436/813; 436/821; 436/824
[58] Field of Search .............. 436/518, 531, 538, 541, 436/542, 548, 808, 810, 815, 821, 824, 804, 813; 435/4, 7, 28, 188, 810

[56] References Cited

U.S. PATENT DOCUMENTS

| | | | |
|---|---|---|---|
| 4,098,876 | 7/1978 | Piasio et al. | 436/500 |
| 4,298,687 | 11/1981 | Maes | 435/7 |
| 4,299,916 | 11/1981 | Litman et al. | 435/6 |
| 4,399,217 | 8/1983 | Holmquist et al. | 435/7 |
| 4,435,504 | 3/1984 | Zuk et al. | 435/7 |
| 4,492,751 | 1/1985 | Boguslaski et al. | 435/7 |

FOREIGN PATENT DOCUMENTS

| | | |
|---|---|---|
| 0062892 | 10/1982 | European Pat. Off. |
| WO80/02460 | 11/1980 | PCT Int'l Appl. |
| WO82/01773 | 5/1982 | PCT Int'l Appl. |

OTHER PUBLICATIONS

*Enzyme-Immunoassay*, Maggio (Ed.)(1980) CRC Press, Inc., Fla., pp. 64 and 233.
Journal of Immunological Methods, 42, No. 1, (1981), pp. 11–15, Elsevier/North-Holland Biomedical Press, NL, M. Uotila et al.
Clinical Chemistry, 29, No. 1, Jan. (1983), pp. 115–119, Washington, U.S., G. De Groote et al.

*Primary Examiner*—Sidney Marantz
*Attorney, Agent, or Firm*—Oblon, Fisher, Spivak, McClelland & Maier

[57] ABSTRACT

The invention relates to a process for the immunoassay of a substance, such as an antigen, a hapten or an antibody.

This process comprises the following stages:

(1) contacting a sample containing the substance to be assayed with a labelled immunoactive reagent specific to said substance, the immunoactive reagent quantity being such that the substance to be assayed is in excess compared with that labelled immunoactive reagent;

(2) contacting at least part of the thus obtained reaction medium with a solid phase, to which is fixed an immunoactive reagent specific to the substance to be assayed;

(3) separating the reaction medium from the solid phase; and (4) determining the labelled immunoactive reagent content of the solid phase.

This process is more particularly applicable to the assaying of lipoprotein and in this case use is made of an antibody labelled by an enzyme, such as the Raifort peroxidase. It is also possible to assay α-foetoprotein by using monoclonal antibodies.

19 Claims, 5 Drawing Figures

COMPETITIVE IMMUNOASSAY PROTOCAL FOR TARGETS INCLUDING LIPOPROTEINS AND ALPHA-FETOPROTEIN

BACKGROUND OF THE INVENTION

The present invention relates to an immunoassay or immunological determination process for antigens, haptens or antibodies, which is more particularly usable for the assaying of plasma proteins, such as lipoproteins.

For a number of years, lipoprotein assaying has developed in order to provide a better evaluation of the existence of a dyslipemia and in particular cardiovascular risks linked with hyperlipemias.

With this aim in mind, the total lipids (triglycerides and cholesterol) circulating in the blood were firstly assayed, but epidemiological studies very quickly revealed that the measurement of these parameters was imprecise. Interest was then attached to certain fractions of these lipids carried by particular apoproteins and, for example, HDL cholesterol and LDL cholesterol were assayed, because they may give more precise information regarding the existence of a dyslipemia.

Lipoproteins are complex molecular compounds of lipids and proteins. One of their essential features is that of having a lower density than the other serum proteins, which makes it possible to separate them from the other proteins and even to classify them by ultracentrifugation.

Thus, these lipoproteins can be classified according to their density and the following fractions can be separated:

(1) chylomicrons with a density below 0.94 g/l, which are the largest and least dense particles consisting of approximately 98% lipids;
(2) very low density lipoproteins with a density of 0.94 to 1.006;
(3) low density lipoproteins with a density of 1.006 to 1.063;
(4) high density lipoproteins with a density of 1.063 to 1.21;
(5) very high density lipoproteins.

However, this empirical classification based on the -physicochemical characteristics of lipoproteins gives very heterogeneous classes based on their composition in proteins. Thus, low density lipoproteins essentially contain apoproteins B, but also apoproteins C and apoproteins E, whilst the high density lipoprotein fraction mainly contains apoproteins $A_1$ and apoproteins $A_2$, but also apoproteins C, apoproteins D and apoproteins E.

Interest was then attached to the part played by these apoproteins in the transport of lipids in order to obtain a better understanding of the relatively complex metabolism of these lipids. It was attempted to show that the assaying of certain of these vector proteins could be a superior indicator in connection with the detection of dyslipemias. In addition, other assaying methods were developed to more accurately determine the amount of certain apolipoproteins contained in the blood plasma.

However, these assaying methods lead to certain problems, due to the high apolipoprotein concentration of blood plasma and the limited variation in the level of the lipoproteins between so-called normal states and so-called pathological states. For example, hereinafter are given the plasma concentrations of lipoproteins and apolipoproteins in male normolipemic patients aged between 25 and 40.

| LIPOPROTEINS mg/100 ml | | APOLIPOPROTEINS mg/100 ml | |
|---|---|---|---|
| VLDL | 80 | Apo-B | 80–100 |
| LDL | 276 | Apo-AI | 120–150 |
| HDL$_2$ | 86 | Apo-AII | 20–80 |
| HDL$_3$ | 254 | Apo-E | 10 |
| HDL$_2$/HDL$_3$ | 0.36 | Apo-CI | 5–10 |
| | | Apo-CII | 3–5 |
| | | Apo-CIII | 15–20 |
| | | Apo-D | 10–20 |
| | | Apo-F | 15 |

Moreover, to obtain a satisfactory sensitivity, immunoassay processes were developed e.g. by radial immunodiffusion, immunoturbidimetry and immunonephelometry by laser beams, as well as radioimmunology or enzymoimmunology, as described by M. Rosseneu, R. Vercaemst, K. K. Steinberg and G. R. Cooper in CLIN. CHEM. 29/3, pp. 427–433 (1983).

However, most of the hitherto developed methods have come up against difficulties making their use far from easy for the routine of a clinical biology laboratory.

Thus, immunoelectrophoresis is a difficultly automatable method. Moreover, the recommended samples (2 μl) are not compatible with series assays.

Nephelometry by laser beams only requires a 1/100 dilution of the samples to be assayed, but makes it necessary to acquire specific, costly equipment. Moreover, problems are encountered when it is wished to assay samples with a very high lipid content.

Assays by radioimmunology or enzymoimmunology make it possible to obtain a good sensitivity, because they were developed for detecting very small quantities of antigens. However, they are not very suitable for assaying lipoproteins, which are present in large quantities in the blood (approximately 1 g/l). The assaying of lipoproteins by these methods makes significant dilutions of the sample necessary and these are incompatible with working in a routine analytical laboratory. Moreover, these dilutions can be the source of major errors.

In addition, an enzymoimmunoassay process for apolipoproteins B has been developed, which only requires a 200×dilutions of the samples. However, the stability of the reagents used in this method cannot be guaranteed beyond a few days, which makes it incompatible with routine working. This method is described in the Journal of Immunological Methods, 21, 1978, pp. 317–324.

SUMMARY OF THE INVENTION

The present invention relates to an immunoassay process making it possible to obtain a very good sensitivity, without requiring high dilutions of the samples to be assayed.

The inventive process for the immunoassaying of a substance with the aid of at least one immunoactive reagent comprises the following stages:

(1) contacting a sample containing the substance to be assayed with a labelled immunoactive reagent specific to said substance, the immunoactive reagent quantity being such that the substance to be assayed is in excess compared with the labelled immunoactive reagent;
(2) contacting at least part of the thus obtained reaction medium with a solid phase, to which is fixed an immunoactive reagent specific to the substance to be assayed;

(3) separating the reaction medium from the solid phase; and (4) determining the labelled immunoactive reagent content of the solid phase.

According to a variant of the process according to the invention, stages (1) and (2) are simultaneously performed by contacting the substance to be assayed simultaneously with the labelled immunoactive reagent and the solid phase to which the immunoactive reagent is fixed.

According to the invention, the substance to be assayed is an antigen, a hapten or an antibody, whilst the immunoactive reagent is a reagent having an immunological activity able to recognise the substance to be assayed and to combine therewith. When the substance to be assayed is an antigen or a hapten the immunoactive reagent is an antibody specific to the antigen or hapten.

In this case, the labelled immunoactive reagent is a labelled antibody, which can be labelled either by a radioelement, or by a fluorescent element, or by an enzyme, e.g. a conjugate compound of an enzyme and an antibody specific to the antigen or hapten to be assayed.

The immunoactive reagent fixed to the said phase is also an antibody, which can be the same as that constituting the labelled antibody. However, the labelled antibody and the antibody fixed to the solid phase can come from different sources, provided that they are both able to recognise the same antigen.

According to a preferred embodiment of the process according to the invention for the assaying of antigens or haptens, at least one of the antibodies used is a monoclonal antibody.

A more detailed description will be given hereinafter of the performance of the process according to the invention for the immunoassaying of an antigen. In this case, in the first stage of the process according to the invention, the antigen to be assayed is labelled by reaction thereof with a labelled antibody specific to said antigen and which is present in a constant quantity, which is such that the antigen is in excess compared with the antibody. Moreover, at the end of this stage, a reaction medium is obtained comprising on the one hand free antigen molecules in excess, and on the other hand antigen molecules bonded to the labelled antibody.

In the second stage, on contacting said reaction medium or part thereof with a solid phase to which is fixed an antibody specific to an antigen to be assayed, there is competition between the antigen molecules bonded to the labelled antibody and the free antigen molecules for the antibody sites fixed to the solid phase. At the end of this stage, the antibody sites available on the solid phase will essentially be occupied by the free antigen molecules and by the antigen molecules bonded to the labelled antibody and the ratio between the fixed free antigen molecules and the antigen molecules bonded to the labelled antibody fixed to said solid phase will depend on the free antigen quantity present in the reaction medium. Thus, the larger the free antigen quantity, the larger the free antigen quantity fixed to the solid phase at the end of the second stage.

As has been shown hereinbefore, it is also possible to simultaneously perform these two stages by contacting the antigen with the labelled antibody specific to said antigen and with the solid phase to which is fixed an antibody specific of the antigen to be assayed. Thus, during the same stage, the labelling of the antigen to be assayed and the fixing of the antigen to the solid phase take place.

In the final stage of the process, the labelled antibody content of the solid phase is determined. This determination more particularly depends on the marker or tracer used. When it is a radioactive element, the radioactivity of the solid phase or possibly the radioactivity of the reaction medium separated from its solid phase is determined. When the marker is an enzyme, the enzyme quantity fixed to the solid phase is colorimetrically detected and the optical density of the medium is determined in a spectrophotometer.

Following this measurement, information is available on the antigen quantity bonded with the labelled antibody, which is fixed to the solid phase and as this quantity depends on the free antigen quantity remaining at the end of the first stage, it is possible to deduce therefrom the antigen quantity in the sample.

In order to obtain this value, assaying firstly takes place of samples having known antigen quantities, in order to establish a standard curve and reference is then made to the latter for determining the antigen content of the sample.

The process according to the invention is particularly advantageous for the assaying of antigens constituted by proteins present in a biological fluid having a relatively high concentration.

Thus, the fact that in the process according to the invention, there is competition between the free proteins and the proteins bonded to the labelled antibody for the sites of an antibody specific to the proteins, makes it necessary to operate with an excess of said proteins in the first stage. Therefore, this process is suitable for the assaying of samples having relatively high concentrations of the proteins to be assayed and it makes it possible to obtain a satisfactory sensitivity without it being necessary to significantly dilute the samples to be assayed.

However, when using so-called in excess immunoassaying methods, the need to operate with an antibody excess during the first stage, whilst said antibody fixed to the solid support is in a limited quantity, requires dilutions of the antigen increasing in proportion with the quantity of the sample to be assayed.

Moreover, in the process according to the invention, it is possible to work with stable reagents and when using an antibody labelled by an enzyme, there is no need to use special, complicated equipment, because it is merely necessary to have a spectrophotometer for performing the final measurement. Moreover, this method makes it possible to obtain a sensitivity equivalent to nephelometry and which is superior to most other assaying methods.

The process according to the invention is applicable to the assaying of different proteins, particularly the assaying of plasma proteins, such as lipoproteins, immunoglobulins, the factors of the complement and the glycoproteins of the serum.

For example, the lipoproteins can be apolipoproteins B, $A_1$, $A_2$, C, D, E, etc and their combinations. The immunoglobulins can be IgG, IgA, IgM, IgD, IgE, etc. The complement factors can be $C_1q$, $C_3c$, $C_4$, $C_5$ or $C_3a$. The glycoproteins of the serum can be orosomucoid, haptoglobulin, alpha-2-macroglobulin, coeruleoplasmin, prealbumin, albumin, transferin, the protein bonding the retinol, alpha-1-antitrypsin, antithrombine-III, antitrypsin inhibitor, hoemopescin, and beta SP.

It is also possible to use the process according to the invention for assaying the circulating immunocomplex, haptoglobin, reactive protein C, placentary lactogenic hormones, alpha-foetoprotein, $C_1$ esterase, $C_1$ esterase inhibitor and $\alpha_1$-antichymotrypsin.

The process according to the invention is of particular interest for carrying out the assaying of lipoproteins present in the blood plasma. In this case, the process comprises the following stages.

(1) contacting a blood plasma sample containing the lipoproteins to be assayed with a conjugate compound of an antibody specific to said lipoproteins and an enzyme in quantities such that the lipoproteins to be assayed are in excess compared with the antibody;

(2) contacting at least part of the thus obtained reaction medium with a solid phase to which is fixed the same antibody specific to the lipoproteins to be assayed;

(3) separating the reaction medium from the solid phase; and (4) determining the enzyme content of the solid phase.

According to a variant of this process, the two stages (1) and (2) are simultaneously performed by contacting the blood plasma sample containing the lipoproteins to be assayed with the conjugate compound of the antibody specific to said lipoproteins and an enzyme, as well as with the solid phase to which is fixed the same antibody specific to the lipoproteins to be dosed. The enzyme used is preferably horsh-radish peroxidase.

When carrying out assaying, a start is made with the assaying of samples having a known lipoprotein content, in order to plot the standard curve giving the optical density (determined at the end of the operation) as a function of the lipoprotein concentration.

Through then referring to this standard curve, it is possible to determine on the basis of the value of the optical density measured on the sample to be assayed, the lipoprotein content of said sample.

The various reagents used for performing the process according to the invention are prepared by conventional processes.

Thus, standard samples with a known lipoprotein concentration are obtained by dilution from human plasma, which is normal from the lipid balance standpoint and which comes from a limited number of donors. The desired lipoproteins are separated by sequential ultracentrifugation using the methods described by Havel, R. J. and Coll (1955), J. Clin, Bioch 34,1, 345–353, Chapman and Coll (1976) Atherosclerosis 25, 267–291.

Generally, the blood is collected from different fasting patients in tubes containing sodium ethylene diamine tetraacetate in a proportion of 1 mg/ml.

The plasma is then separated by centrifuging for 20 minutes at 2500 g and the density of the solvent is adjusted to 1.050 with NaCl. Centrifuging then takes place in an ultracentrifuge by carrying out several stages in such a way as to obtain fractions with densities ranging between 1.025 and 1.050. On the basis of these fractions, the desired lipoproteins are separated by conventional methods, e.g. by ultracentrifugation in the case of lipoproteins B and the lipoprotein solution is calibrated by a precise analytical method.

The antibody specific to the lipoproteins is prepared from the aforementioned separated lipoproteins, which are used for obtaining immunoglobulins specific to human antilipoproteins by immunization in an animal such as the rabbit, sheep, etc. The immunoglobulins are obtained from the serum of the immunized animal, are purified by precipitation with caprylic acid and separated by centrifuging. The supernatant substance is recovered by filtering and dialyzed overnight at 4° C. against an acetate buffer. The solution is then filtered and its purity is tested by electrophoresis.

The conjugate compound of the enzyme and the specific antibody of the lipoproteins to be assayed is produced according to conventional methods, e.g. using the periodate method described by Wilson B. M. and Nakane P. K. in "Recent developments in the periodate method of conjugating horseradish peroxidase (HRPO) to antibodies"—Knapp W, Holubar K and Wick G (publishers)—"Immunofluorescence and related staining techniques", New York: Elsevier/North Holland Biomedical Press, 1978, p. 216, when the enzyme is the horse-radish peroxidase, followed by purification by filtration on gel.

For performing the process according to the invention, the solid phase to which the antibody is fixed is generally constituted by a bladed device located within a plastic tube. This device is generally made from polyamide and the antibody is fixed thereto by introducing into the tube a solution of human antilipoprotein purified immunoglobulins obtained e.g. in the sheep and by leaving this solution in contact with the blades for approximately 4 hours. Preferably, the immunoglobulins have previously been activated by the method described by Eiji Ishikawa, Yoshitaka Hamagucki, Masayoshi Imagawa (III,8-preparation of antibody coated polystyrene balls for sandwich enzyme immunoassay pp. 119–122 Enzyme Immunoassay Ishikawa, Kawai, Miyai Igahushoim, Tokyo, 1981.

Several tubes containing the desired antibody quantity can be prepared in this way.

When the enzyme used for labelling of the antibody is the horse-radish peroxidase, the enzymatic detection is carried out by means of a chromogen, which is reconstituted at the time of use from a powder obtained by lyophilization of an orthophenylene diamine solution in sodium phosphate.

For the first stage of the process according to the invention, it is possible to use a plastic tube having no bladed device or the previously described bladed device-equipped tube modified so as to have in its upper part a synthetic material dome positioned above the bladed device to which the antibody is fixed. This dome must be easy to perforate, so as to permit the outflow of the reaction medium onto the solid phase at the end of the first stage, i.e. onto the bladed device present in the lower part of the tube. Tubes having a bladed device usable in the process according to the invention have more particularly been described in French Patent EN No. 78/050040 filed in the name of the Commissariat a l'Energie Atomique.

The various reagents and equipment usable for the immunoassay according to the invention can be placed in a kit comprising:

a system of tubes, each having a solid phase, e.g. a bladed device, coated under the same conditions with human antilipoprotein immunoglobulins, said tubes being kept protected from moisture in adequate blister-type packs;

a series of bottles containing standard samples covering the lipoprotein range 0.1 to 0.005 g/l, which can be stored in liquid form with the addition of adequate stabilizers, such as antibiotics, antioxidants and a protease inhibitor, or in lyophilization form, lyophilization being carried out in the presence of sucrose;

a bottle containing the conjugate compound resulting from the coupling of human antilipoprotein immunoglobulins with an enzyme, such as the horse-radish peroxidase, said compound being possibly prediluted in a borate buffer containing delipoproteinated sheep serum and a preservative, such as thimerosal, in liquid or lyophilized form; and a bottle containing a chromogen for enzymatic detection, said chromogen being possibly in lyophilized form and in this case the kit also has a bottle containing a chromogen dilution buffer.

Thus, the kit contains all the elements necessary for plotting the standard calibration curve and the assaying of the samples.

The process according to the invention can also be used for α-foetoprotein immunoassay. The α-foetoprotein is a glycoprotein synthesized by the cells of the fetal liver and the yolk sac. It is the major constituent of the fetal serum. It is also found in the amniotic fluid and in the maternal serum. In the amniotic fluid, the maximum level is reached at about the 15th week (20 to 50 μg/ml) and in the maternal serum towards the 34th week (>200 ng/ml). The use of α-foetoprotein assaying is particularly useful in the following cases.

In obstetrics, α-foetoprotein permits the antinatal diagnosis of deformities of the neural tube by assays on the maternal blood, then on the amniotic fluid at about the 16th to 18th week of pregnancy. In addition, an exaggerated α-foetoprotein level can indicate fetal pain and a multiple pregnancy, whilst a low level can suggest toxemia, retarded growth or a placentary tumor.

In cancerology, α-foetoprotein assists diagnosis and makes it possible to post-therapeutically follow hepatocellular carcinomas, particularly cirrhosis, teratocarcinomas of all localizations, but particularly ovarian, testicular and sacrococcygeal and hepatic metastases of various other cancers, particularly digestive cancers.

In hepatology, α-foetoprotein proves an intense regeneration process in viral hepatitis cases.

In pediatrics, α-foetoprotein makes it possible to differentiate between biliary atresia and neonatal hepatitis and also confirms a hereditary tyrosinosis.

The process according to the invention for assaying the α-foetoprotein, in a sample of amniotic fluid, serum or plasma comprises the following stages:

(1) contacting the sample containing the α-foetoprotein to be assayed with a conjugate compound of an antibody specific to the α-foetoprotein to be assayed and an enzyme, in a quantity such that the α-foetoprotein to be assayed is in excess compared with the antibody;

(2) contacting at least part of the thus obtained reaction medium with a solid phase to which is fixed an antibody specific to the α-foetoprotein to be assayed;

(3) separating the reaction medium from the solid phase; and (4) determining the enzyme content of the solid phase.

According to a variant of this process, stages (1) and (2) are simultaneously performed by contacting the sample containing the α-foetoprotein to be assayed with the conjugate compound of the antibody specific to the α-foetoprotein and an enzyme, as well as with the solid phase to which is fixed an antibody specific to the α-foetoprotein to be assayed.

According to a preferred manner of performing this process, the antibody of the conjugate compound is a monoclonal antibody and the antibody fixed to the solid phase is an anti α-foetoprotein immunoglobulin. Preferable, the enzyme used is the horse-radish peroxidase.

As in the case of assaying lipoproteins, the elements necessary for performing this assay can be placed in a kit comprising:

a system of tubes each having a solid phase coated under the same conditions with human anti α-foetoprotein immunoglobulins;

a series of bottles containing standard samples having the α-foetoprotein range of 50 to 1000 ng/ml;

a bottle containing the conjugate compound resulting from the coupling of a monoclonal antibody specific to the α-foetoprotein with an enzyme; and a bottle containing a chromogen for enzymatic detection.

As in the case of assaying lipoproteins, the tubes can have a solid phase constituted by a bladed device and the chromogen can be in lyophilized form. In the latter case, the kit also includes a bottle containing a chromogen dilution buffer.

BRIEF DESCRIPTION OF THE DRAWINGS

The invention is described in greater detail hereinafter relative to non-limitative embodiments illustrating the performance of the process according to the invention for apolipoprotein B assaying and α-foetoprotein assaying and with reference to the attached drawings, wherein show.

DETAILED DESCRIPTION OF THE PREFERRED EMBODIMENTS

It can be seen from FIG. 1 that the assaying device used in the following examples is constituted by an almost cylindrical transparent tube 1 having a circular section and closed at the bottom by a flat base 3. From the bottom, the tube successivey has a first reaction zone A, in which is engaged and secured a part 5 for fixing the antibody specific to the protein to be assayed. This part is constituted by a solid cylindrical sleeve 5a, whereof the lower end rests on base 3 of tube 1 and longitudinal blades 5b, whose outer edges come into contact with the inner surface 1a of tube 1. This makes it possible to secure the part in the tube, because said part is made from an elastic material, e.g. polyamide. The height of part 5 determines the height of reaction zone A of tube 1.

As can be seen from the drawing, through having a flat base 3 it is possible to limit the quantities of reagent to be used, which must be just sufficient to completely immerse part 5. Above the first reaction zone A, the tube has a second reading zone B, followed by a zone C of greater height for carrying out the washing stages. In the second reading zone B, the tube has a very good optical quality obtained more particularly as a result of the fact that the inner surface 1a and the outer surface 1b of the wall of tube 1 are well centered relative to one another in said zone. Thus, in said tube zone, the wall thickness is homogeneous and constant.

Tube 1 is made from a plastic material, e.g. polymethyl methacrylate and is perferably obtained by injection moulding.

EXAMPLE 1

Assaying apolipoproteins B

For carrying out this assay, firstly a range of 6 standard samples is prepared having known lipoprotein B concentrations ranging from 0.5 to 0.005 mg/ml by ½, 1/10, 1/20, 1/50, 1/100 and 1/200 dilutions of a mother 1 g/l lipoprotein B solution in a 0.05 M borate buffer, pH=8, 150 mM, NaCl, 20 nM KCl, also containing 15% (v/v) of normal sheep serum delipoproteinated by ultracentrifugation.

The antibodies specific to the human lipoproteins B is obtained by immunization of a sheep using human lipoproteins B identical to those used for the preparation of the standard samples. The immunoglobulins are obtained from the serum of the immunized sheep and are purified by precipitation with caprylic acid, separated by centrifuging, recovery of the supernatant product by filtering, dialysis of the supernatant product overnight at 4° C. against a 0.1 M acetate buffer at pH 5.7. The solution is then contacted for 15 minutes with DEAE A 50 gel at a rate of 50 g of buffer DEAE A 50 (in the same solution) per gram of proteins. By filtering, a solution is collected containing immunoglobulins, whose purity can be tested by electrophoresis.

The conjugate compound of the antibodies specific to the lipoproteins B and an enzyme is then prepared by coupling the thus obtained immunoglobulins and the enzyme constituted by the Boehringer horse-radish peroxidase (grade 1 R.Z=3) in accordance with the sodium periodate method described by Wilson and Nakane. The thus obtained conjugate compound is then purified by filtering on gel, using Ultrogel Ac A 44 and carrying out elution by a PBS buffer (50 mM; pH=7.2). This purification essentially makes it possible to eliminate the free enzyme traces which could considerably interfere with the assaying operation. The thus obtained conjugate compound is then diluted 1/200 in a 0.05 M borate buffer ; pH=8.0, 150 mM NaCl, 20 mM KCl, also containing 15% (v/v) of normal sheep serum delipoproteinated by ultracentrifugation.

Figure 1:
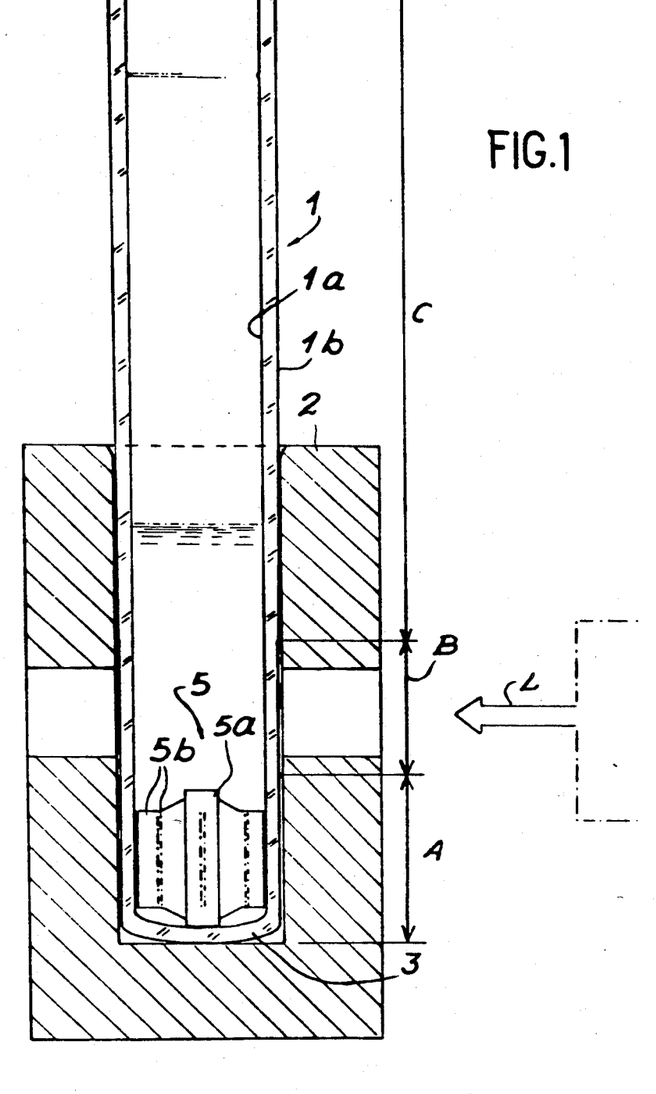
FIG. 1 diagrammatically in vertical section, an assaying device according to the invention.

For assaying purposes, use is made of polymethyl methacrylate tubes as shown in FIG. 1 and at the bottom of which are engaged and secured bladed devices made from polyamide, to which are fixed the antibodies specific to the lipoproteins B.

To fix these antibodies to the solid phase constituted by the bladed device of the tube, into the latter is introduced 1 ml of 50 μg/ml immunoglobulin solution in a phosphate buffer (0.0 M; pH=7.0) for 4 hours at ambient temperature, using immunoglobulins obtained in the sheep after activating them according to the process described by Eiji Ishikawa, Yoshitaka Hamaguchi and Masayoshi Imagawa. After 4 hours, the tube is washed 3 times with the phosphate buffer, dried in vacuo at 37° C. and then kept at 4° C. protected from moisture.

Assaying is then performed in the following way. Into a first plastic tube without a bladed device is introduced 0.05 ml of standard sample or sample to be assayed and 0.5 ml of the conjugate compound prediluted to 1/200 in the borate buffer and incubation is allowed to take place at ambient temperature. Following 90 minutes incubation, the content of the first tube or at least part thereof (at least 0.450 ml) is poured into one of the plastic tubes, whose bladed device is coated with the antibody specific to the lipoproteins B and the liquid medium is kept in contact with the blades for 2 hours at ambient temperature. The liquid phase of the tube is then sucked up and the tube is firstly washed with soft water containing 0.1% of Tween 20 and then twice with soft water. These washing operations are carried out by filling the tube with 2 ml of liquid and then emptying it by suction.

Following these washing operations, 0.5 ml of the chromogen solution reconstituted just prior to use by adding 16 ml of a buffer containing 0.92% (v/v) of homohydrated citric acid, 0.01% (wt/v) of thimerosal and 0.02% (v/v) of 30% $H_2O_2$ (Merck) to a mixture obtained by lyophilization of a 10 mg/ml orthophenylene diamine solution 2HCl (Sigma) in 3.2 ml of phosphate ($Na_2HPO_4$, $2H_2O$ at 100 mg/ml), is poured into the tube. Development of the enzymatic reaction is allowed to take place for 30 minutes at ambient temperature and the process is stopped by adding 2 ml of 1N oxalic acid solution. The optical density of the solution is then determined by spectrophotometry at 492 nm by introducing tube 1 into spectrophotometer 2 in such a way that the light beam L passes through tube 1 level with its reading zone B.

Figure 2:
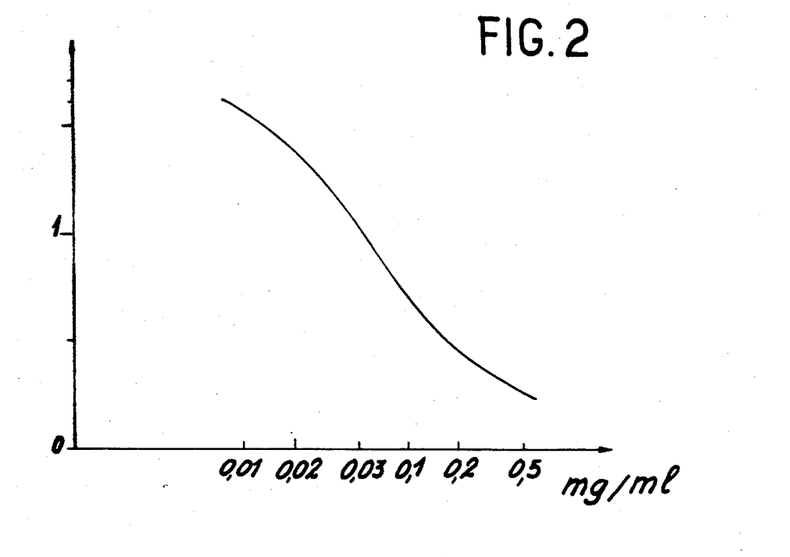
FIGS. 2 and 3 standard curves for assaying lipoproteins B obtained by the process according to the invention.

The assaying operations are repeated for all the standard samples and the results obtained are given in table I and in FIG. 2, which shows the standard curve giving the optical densities as a function of the lipoprotein B content of the samples.

The same assaying operations are carried out on the sample to be assayed and the standard curve is marked to show the lipoprotein B concentration to which corresponds the optical density measured on said sample.

TABLE I

| Dilution | Concentration (in mg/ml) | O.D. |
|---|---|---|
| 1/2 | 0.5 | 0.28 |
| 1/5 | 0.2 | 0.49 |
| 1/10 | 0.1 | 0.74 |
| 1/20 | 0.05 | 1.01 |
| 1/50 | 0.02 | 1.42 |
| 1/100 | 0.01 | 1.60 |

EXAMPLE 2

Assaying apolipoproteins

For carrying out these assays, as in the case of example 1, a range of 6 standard samples are prepared which have known lipoprotein B concentrations ranging from 0.5 to 0.01 mg/ml by 1/2, 1/5, 1/10, 1/20, 1/50 and 1/100 dilutions of a 1 g/l lipoprotein B mother solution in a 0.05 M borate buffer, pH=8, 150 mM NaCl, 20 mM KCl, also containing 15% (v/v) of normal sheep serum delipoproteinated by ultracentrifugation.

For the purpose of this assay, use is made of the same tubes, the same antibody and the same conjugate compound as in example 1, the antibody being fixed to the solid phase constituted by the bladed device of the tube. The assay is then carried out in the following manner.

Into the tube containing the bladed device to which the antibody is fixed is introduced 100 μl of standard sample and 1 ml of the conjugate compound prediluted to 1/2000 and incubation is allowed to take place for 2 h at 37° C. Suction then takes place of the liquid phase of the tube and the latter is washed as in example 1. Enzymatic detection of the solid phase takes place under the same conditions as in example 1 and the same products are used.

Figure 3:
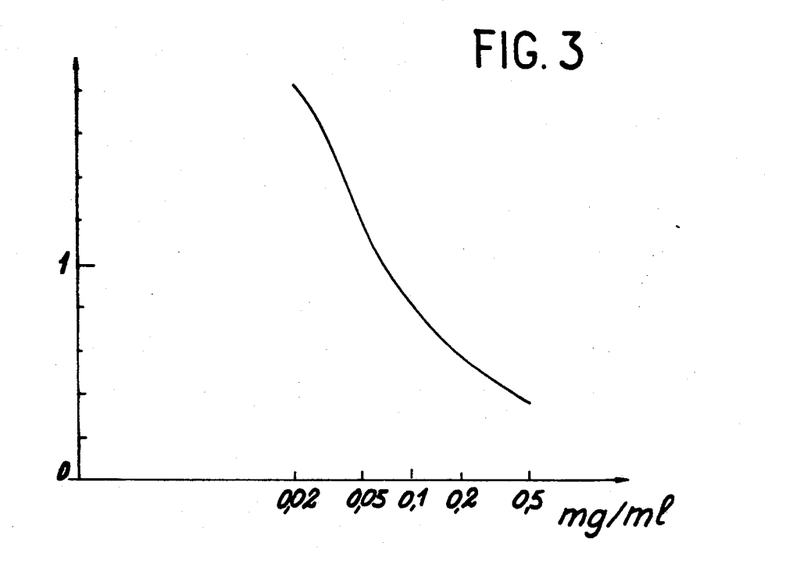

The assaying operations are repeated for all the standard samples. The results are given in table 2 and in FIG. 3, which shows the standard curve giving the optical densities as a function of the lipoprotein B content of the samples. The same assaying operations are also carried out on the sample to be assayed, but using 10 μl of sample and 1 ml of the conjugate compound prediluted to 1/2000.

TABLE 2

| Dilution | Concentration (in mg/ml) | O.D. |
|---|---|---|
| 1/2 | 0.5 | 0.35 |
| 1/5 | 0.2 | 0.58 |
| 1/10 | 0.1 | 0.84 |
| 1/20 | 0.05 | 1.24 |
| 1/50 | 0.02 | 1.850 |
| 1/100 | 0.01 | 2.000 |

EXAMPLE 3

Assaying lipoproteins B

For comparison, hereinafter are given the results obtained with a conventional immunoenzymatic assaying method using the same reagents, but involving the following stages.

1. Incubation of the standard sample or the sample to be assayed with the solid phase to which the antibody is fixed 0.5 ml of standard sample prediluted to 1/100, 1/500, 1/1000, 1/2000, 1/4000, 1/5000, 1/10000, 1/20000 is incubated for 1 hour at ambient temperature in tubes containing the bladed device, coated with antibodies specific to the lipoproteins B. The tube content then undergoes suction and is washed with a 0.1% Tween 20 solution, followed by 2 washings with soft water.

2. Incubation of the conjugate compound 0.5 ml of the 1/1500 diluted horse-radish peroxidase-human antilipoprotein antibody conjugate compound is then introduced into the tube and incubation is allowed to take place for 2 hours at ambient temperature. The liquid phase then undergoes suction and the tube is washed as hereinbefore, firstly with 0.1% Tween 20 and then twice with soft water.

3. Assaying the enzyme fixed to the solid phase

Figure 4:
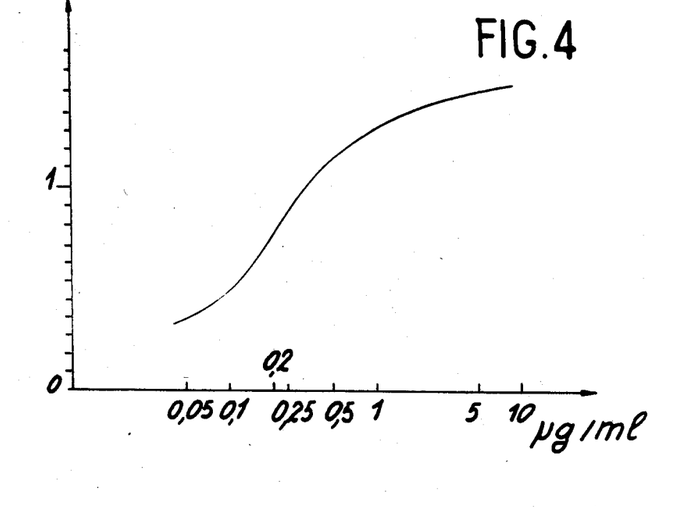
FIG. 4 the standard curve of the assay of lipoproteins B obtained by a prior art process.

Enzymatic detection takes place by adding the same chromogens and under the same conditions. Reading also takes place at 492 nm. The results obtained are given in the following table 3 and in FIG. 4, which shows the standard curve obtained under these conditions.

Using this conventional method, a sample to be assayed must be diluted 1/5000 or 1/10,000, whereas in the process according to the invention, the sample need not undergo a prior dilution if it is 20 μl, or need only be 1/25 or 1/50 diluted in the case of 1 ml.

TABLE 3

| Dilution | Concentration (in μg/ml) | O.D. |
|---|---|---|
| 1/100 | 10 μg/ml | 1.70 |
| 1/500 | 5 | 1.65 |
| 1/1000 | 1 | 1.50 |
| 1/2000 | 0.5 | 1.32 |
| 1/4000 | 0.25 | 1.05 |
| 1/5000 | 0.2 | 0.85 |
| 1/10000 | 0.1 | 0.51 |
| 1/20000 | 0.050 | 0.37 |
| blank | | 0.16 |

EXAMPLE 4

Assaying α-foetoprotein

This example illustrates α-foetoprotein assaying by the process according to the invention using as the first antibody a monoclonal antibody specific to α-foetoprotein and as the second antibody fixed to the solid phase human anti-α-foetoprotein immunoglobulins obtained from the goat.

Firstly, a range of 4 standard samples is prepared with known α-foetoprotein concentrations between 50 and 1000 ng/ml obtained by the dilution of amniotic fluids in a phosphate buffer (50 mM; pH=7.4) and also containing 5% (v/v) of normal sheep serum and 0.01% (v/v) of thimerosal.

Use is made of a monoclonal antibody K6B$_1$ obtained by melting BALB/C mouse splenocytes immunized with human α-foetoprotein and myeloma cells in accordance with a procedure derived from that of Kohler G. and Milstein C., described by Sertour J., Bellet D., Salard J. L. and Marchand J. "Polyclonal or Monoclonal antibodies in an AFP assay. Protides of the Biological Fluids. 31st Colloquium", Brussels 1983, publishers Dr H. Peeters-Pergamon Press Oxford and New York.

This is followed by the preparation of the conjugate compound of monoclonal antibody specific to the α-foetoprotein and an enzyme by coupling the monoclonal antibody with horse-radish peroxidase in accordance with the procedure used in example 1. The conjugate compound is also purified under the same conditions as in example 1, followed by a 1/20000 dilution thereof in a phosphate buffer (50 mM; pH=7.4), also containing 5% (v/v) of normal sheep serum and 0.01% of thimerosal.

In order to carry out the assay, use is made of the polystyrene tubes shown in FIG. 1, at the bottom of which is engaged and secured a polyamide bladed device, to which is fixed the second antibody specific to the α-foetoprotein.

In order to fix this antibody to the solid phase constituted by the bladed device of the tube, into the tube is introduced 1 ml of 50 μg/ml immunoglobulin solution in a phosphate buffer (0.05M; pH=7.0) for 4 hours at ambient temperature, using anti-α-foetoprotein immunoglobulins obtained in the goat after activating them according to the process described by Eiji Ishikawa, Yoshitaka Hamaguchi and Masayoshi Imagawa.

After 4 hours, the tube is washed 3 times with the phosphate buffer, then dried in vacuo at 37° C., followed by storage at 4° C. protected from moisture.

The assay is then carried out in the following way. 0.5 ml of standard sample or sample to be assayed and 0.5 ml of the conjugate compound prediluted to 1/20,000 in the phosphate buffer is introduced into a first plastic tube without a bladed device and incubation takes place at 37° C. Following incubation for 90 minutes, the content of this first tube or at least part of it (at least 0.450 ml) is poured into one of the plastic tubes, whereof the bladed device is coated with the specific antibody constituted by anti-α-foetoprotein immunoglobulins obtained from the goat. The liquid medium is kept in contact with the blades for 1 hour at 37° C. This is followed by suction of the liquid phase of the tube and the latter is firstly washed with soft water containing 0.1% of Tween 20 and then twice with soft water.

Following these washing operations, into the tube is poured 0.5 ml of the chromogen solution used in example 1 and enzymatic detection is carried out under the same conditions as in example 1.

Figure 5:
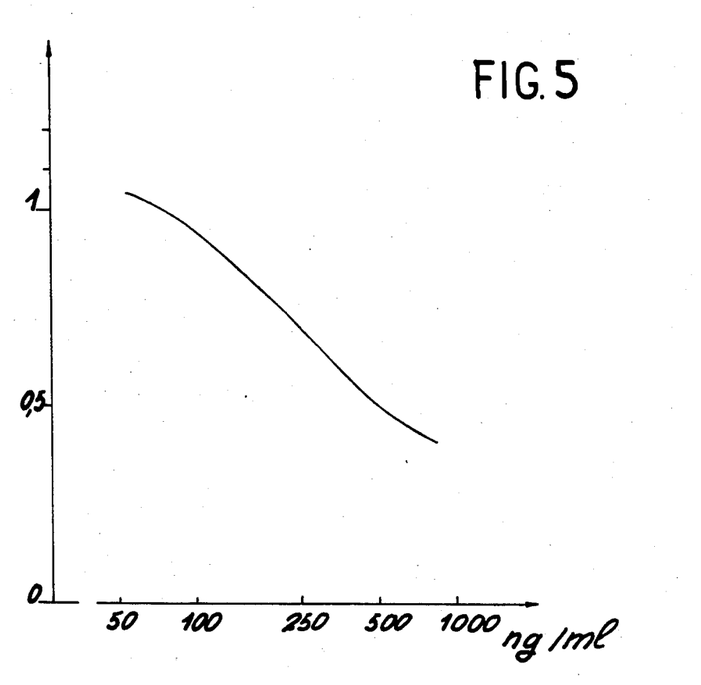
FIG. 5 the standard curve of the assay of α-foetoprotein obtained by using monoclonal antibodies according to the process of the invention.

The results obtained are given in FIG. 5, which shows the standard curve obtained under these conditions.

What is claimed is:

1. A process for the immunological determination of a substance, which comprises the following steps:
    (1) contacting a sample containing the substance to be determined with a labelled immunoactive reagent specific to said substance, the immunoactive reagent quantity being such that the substance to be determined is in excess compared with that labelled immunoactive reagent;
    (2) contacting at least part of the reaction medium obtained in step (1) with a solid phase, to which is fixed a limited amount of an immunoactive reagent specific to the substance to be determined, whereby the excess unlabeled substance and the substance combined with the labeled immunoactive reagent resulting from step (1) compete for limited binding sites of the immunoactive reagent fixed to the solid phase;
    (3) separating the reaction medium from the solid phase;
    (4) determining the labelled immunoactive reagent content of the solid phase; and
    (5) relating the determination of step (4) to a standard curve to determine the substance content of said sample.

2. A process according to claim 1, wherein steps (1) and (2) are simultaneously performed by contacting the substance to be assayed simultaneously with the labelled immunoactive reagent and with the solid phase to which said reagent is fixed.

3. A process according to claim 1, wherein the substance to be determined is a plasma protein selected from the group consisting of lipoprotein, immunoglobulins, complement factors and glycoproteins.

4. A process according to claim 1 wherein the substance to be determined is an antibody.

5. A process according to claim 1, wherein the substance to be determined is an antigen or a hapten.

6. A process according to claim 5, wherein the labelled immunoactive reagent is an antibody labelled by radioactive element.

7. A process according to claim 5, wherein the labelled immunoactive reagent is a conjugate compound of an enzyme and an antibody specific to the antigen or hapten to be determined.

8. A process according to claim 5, wherein the labelled immunoactive reagent is an antibody labelled by a fluorescent element.

9. A process according to claim 3, wherein at least one of the immunoactive reagents is a monoclonal antibody.

10. A process for the immunological determination of lipoproteins in blood plasma, which comprises the following steps:
    (1) contacting a blood plasma sample containing the lipoproteins to be determined with a conjugate compound of an antibody specific to said lipoproteins and an enzyme, the conjugate quantity being such that the lipoproteins to be determined are in excess compared with the antibody;
    (2) contacting at least part of the reaction medium obtained in step (1) with a solid phase to which is fixed a limited amount of the same antibody specific to the lipoproteins to be determined as the antibody used in the conjugate compound of step (1), whereby the excess unlabelled lipoproteins and the lipoproteins combined with the conjugate compound resulting from step (1) compete for limited binding sites of the antibody fixed to the solid phase;
    (3) separating the reaction medium from the solid phase;
    (4) determining the enzyme content of the solid phase; and
    (5) relating the determination of step (4) to a standard curve to determine the lipoprotein content of said sample.

11. A process according to claim 10, wherein steps (1) and (2) are simultaneously performed by contacting the blood plasma sample containing the lipoproteins to be determined simultaneously with the conjugate compound of an antibody specific to these lipoproteins and an enzyme, as well as with the solid phase to which is fixed the same antibody specific to the lipoproteins to be determined.

12. A process according to either of the claims 10 or 11, wherein the enzyme is the horse-radish peroxidase.

13. A kit for determining lipoproteins by performing the process according to claim 10, which comprises:
    a series of tubes each containing a solid phase which has been coated with anti-human antilipoprotein immunoglobulins;
    a series of bottles containing standard lipoprotein samples covering the range 0.1 to 0.005 g/l;
    one bottle containing a conjugate compound resulting from the coupling of anti-human antilipoprotein immunoglobulins with an enzyme; and
    a bottle containing a chromogen for enzymatic detection.

14. A kit according to claim 13, wherein the kit also comprises a bottle containing a chromogen dilution buffer.

15. A process for the immunological determination of α-foetoprotein (α-foetoprotein, present in a sample of serum, plasma or amniotic fluid, which comprises the following steps:
    (1) contacting the sample containing the α-foetoprotein to be determined with a conjugate compound of an antibody specific to the α-foetoprotein to be determined and an enzyme, the conjugate quantity being such that the α-foetoprotein to be determined is in excess compared with the antibody;
    (2) contacting at least part of the reaction medium obtained in step (1) with a solid phase to which is fixed a limited amount of an antibody specific to the α-foetoprotein to be determined, whereby the excess unlabelled α-foetoprotein and the α-foetoprotein combined with the conjugate compound resulting from step (1) compete for limited binding sites of the antibody fixed to the solid phase;
(3) separating the reaction medium from the solid phase; and
(4) determining the enzyme content of the solid phase; and
(5) relating the determination of step (4) to a standard curve to determine the α-foetoprotein content of said sample.

16. A process according to claim 15, wherein steps (1) and (2) are simultaneously performed by contacting the sample containing the α-foetoprotein to be determined simultaneously with the conjugate compound of an antibody specific to the α-foetoprotein to be determined and an enzyme, as well as with the solid phase to which is fixed an antibody specific to the α-foetoprotein to be determined.

17. A process according to claim 15, wherein the antibody of the conjugate compound is a monoclonal antibody.

18. A process according to claim 15, wherein the antibody fixed to the solid phase is an anti-α-foetoprotein immunoglobulin.

19. A process according to claim 15, wherein the enzyme is the horse-radish peroxidase.

* * * * *